US009375461B2

(12) United States Patent
Rombi

(10) Patent No.: US 9,375,461 B2
(45) Date of Patent: Jun. 28, 2016

(54) COMPOSITION COMPRISING A COMBINATION OF AT LEAST ONE PROTEOLYTIC ENZYME AND AT LEAST ONE LIPOLYTIC ENZYME, FOR USE IN PREVENTING TRIGLYCERIDE SYNTHESIS

(71) Applicant: IMARKO RESEARCH S.A., Luxembourg (LU)

(72) Inventor: Max Rombi, Bordighera (IT)

(73) Assignee: IMARKO RESEARCH S.A., Luxembourg (LU)

( * ) Notice: Subject to any disclaimer, the term of this patent is extended or adjusted under 35 U.S.C. 154(b) by 0 days.

(21) Appl. No.: 13/900,084

(22) Filed: May 22, 2013

(65) Prior Publication Data

US 2013/0323219 A1 Dec. 5, 2013

Related U.S. Application Data

(63) Continuation of application No. 13/519,534, filed as application No. PCT/EP2011/069045 on Oct. 28, 2011.

(30) Foreign Application Priority Data

Oct. 29, 2010 (FR) ...................................... 10 58957

(51) Int. Cl.
*A61K 38/48* (2006.01)
*A61K 38/43* (2006.01)
*A61K 38/46* (2006.01)

(52) U.S. Cl.
CPC ............. *A61K 38/482* (2013.01); *A61K 38/465* (2013.01)

(58) Field of Classification Search
CPC ................................. A61K 38/48; A61K 38/43
See application file for complete search history.

(56) References Cited

U.S. PATENT DOCUMENTS

| 5,223,425 | A | 6/1993 | Flier et al. |
| 6,011,001 | A | 1/2000 | Navia et al. |
| 6,699,496 | B1 * | 3/2004 | Kojima et al. ............... 424/439 |
| 2003/0095961 | A1 | 5/2003 | Houston et al. |
| 2005/0003027 | A1 | 1/2005 | Diaz et al. |
| 2005/0059567 | A1 | 3/2005 | Showell et al. |
| 2009/0299093 | A1 * | 12/2009 | Evans et al. ................... 562/553 |

FOREIGN PATENT DOCUMENTS

| CN | 1634351 A | 7/2005 | |
| DK | WO 2006/136160 A2 * | 12/2006 | ............. A61K 38/48 |
| EP | 1459738 A1 | 9/2004 | |
| FR | 2 758 143 | 7/1998 | |
| GB | 2396297 A | 6/2004 | |
| GB | 2 465 814 A | 6/2010 | |
| JP | 8-225460 A | 9/1996 | |
| JP | 2000-226335 A | 8/2000 | |
| JP | 2001-220134 A | 8/2001 | |
| JP | 2004-115434 A | 4/2004 | |
| RU | 2 219 239 C2 | 12/1997 | |
| WO | WO 94/20610 A1 | 9/1994 | |
| WO | WO 03/066088 A2 | 8/2003 | |
| WO | WO 2006/044529 A1 | 4/2006 | |
| WO | WO 2006/136160 A2 | 12/2006 | |
| WO | WO 2007/047205 A2 | 4/2007 | |
| WO | WO 2007/100675 A2 | 9/2007 | |
| WO | WO 2008/019417 A2 | 2/2008 | |
| WO | WO 2008/045148 A2 | 4/2008 | |
| WO | WO 2009/120760 A1 | 10/2009 | |
| WO | WO 2010/025126 A1 | 3/2010 | |
| WO | WO 2010/080830 A1 | 7/2010 | |
| WO | WO 2010/080835 A1 | 7/2010 | |
| WO | WO 2010/134806 A1 | 11/2010 | |

OTHER PUBLICATIONS

Christophe et al., "Fat Digestion and Absorption", The American Oil Chemists Society, 2000, pp. 134-135.
Cunnane, "Survival of the Fattest (The Key to Human Brain Evolution)", World Scientific Publishing, 2005, pp. 205-208 (7 pages provided).
English Translation of PCT/EP2011/069045 drawings and certificate of Translation.
Johnston, "Gastrointestinal Tissue", 1977, pp. 151-187.
Kaplan, "The Deadly Quartet", Arch Intern Med, vol. 149, Jul. 1989, pp. 1514-1520.
Neel, "Diabetes Mellitus: A Thrifty Genotype Rendered Detrimental by Progress?", American Journal of Human Genetics, 1962, pp. 353-362.
PCT/ISA/210—International Search Report mailed Apr. 2, 2012, issued in PCT/EP2011/069045.
Reaven, "Syndrome X: 6 years later", Journal of Internal Medicine, vol. 236 (Supplement 736), 1994, pp. 13-22.
Reaven, "Syndrome X: Overcoming the Silent Killer That Can Give You a Heart Attack", Simon & Schuster, 2000, pp. 42-55 (10 pages provided).
Rogalska et al., "Stereoselective Hydrolysis of Triglycerides by Animal and Microbial Lipases", Chirality, vol. 5, 1993, pp. 24-30.
Kharkevich: Pharmacology, Moscow, pp. 372-373, 8th edition (corresponding to p. 250 of the 1st edition of 1980).
Setala, "The promise of Enzymes in Therapy of Hyperlipidemia", Medical Hypotneses 20: pp. 287-315, 1986.
Sugihara et al., "Characterization of Geotrichum candidum lipase III with some preference for the inside ester bond of triglyceride", Appl Microbiol Biotechnol, 1993, 40, pp. 279-283.
Tanaka et al., "Role of Endothelial Lipase in Plasma HDL Levels in a Murine Model of Hypertriglyceridemia", Journal of atherosclerosis and thrombosis, vol. 16, No. 4, pp. 327-338, 2009.

(Continued)

*Primary Examiner* — Karen Cochrane Carlson
*Assistant Examiner* — Natalie Moss
(74) *Attorney, Agent, or Firm* — Birch, Stewart, Kolasch & Birch, LLP

(57) ABSTRACT

The present invention relates to a composition comprising a combination of at least one proteolytic enzyme, such as subtilisin, and at least one lipolytic enzyme, for use in preventing triglyceride synthesis, advantageously by degrading 2-monoacylglycerol in the intestine. The invention also has as an object such a composition for use as a drug, cosmetic agent, medical device, dietary composition, dietary supplement or nutraceutical, notably for use in preventing or treating obesity, atherosclerosis, type 2 diabetes or for use in preventing or reducing excess weight.

11 Claims, 2 Drawing Sheets

(56) References Cited

OTHER PUBLICATIONS

Woolley and Petersen, extract from the book "Lipases: their structure, Biochemistry and application", Apr. 14, 1994, Chapter 15: "Medical aspects of triglycerides lipases" by Bengtsson-Olivecrona and Olivecrona.

Zock et al., "Partial conservation of the sn-2 position of dietary triglycerides in fasting plasma lipids in humans", European Journal of Clinical Investigation, 1996, 26, pp. 141-150.

Suzuki et al., "Effect of oral administration of nattokinase extract on blood mobility," Journal of Analytical Bio-Science, vol. 25, 2002, No. 4, pp. 333-338.

Matsuo, "Health Benefits of Dietary Diacylglycerol in Practiai Use", Chapter 16 of the book "Dietary fats and Risk of Chronic Disease", (2006) pp. 229-242.

* cited by examiner

COMPOSITION COMPRISING A COMBINATION OF AT LEAST ONE PROTEOLYTIC ENZYME AND AT LEAST ONE LIPOLYTIC ENZYME, FOR USE IN PREVENTING TRIGLYCERIDE SYNTHESIS

The present application is a 37 C.F.R. §1.53(b) continuation of, and claims priority to, U.S. application Ser. No. 13/519,534, filed Jun. 27, 2012. Application Ser. No. 13/519,534 is the national phase under 35 U.S.C. §371 of International Application No. PCT/EP2011/069045, filed on Oct. 28, 2011. Priority is also claimed to French Application No. 1058957 filed on Oct. 29, 2010. The entire contents of each of these applications is hereby incorporated by reference.

The present invention relates to a composition comprising a combination of at least one proteolytic enzyme, such as subtilisin, and at least one lipolytic enzyme, for use in preventing triglyceride synthesis, advantageously by degrading 2-monoacylglycerol in the intestine. Advantageously, the composition of the present invention comprises several lipases. The invention also relates to such a composition for use as a drug, cosmetic agent, medical device, dietary composition, dietary supplement or nutraceutical, notably for use in preventing or treating obesity, atherosclerosis, type 2 diabetes or for use in preventing or reducing excess weight.

It is generally acknowledged today that the increase in the frequency of excess weight and obesity, type 2 diabetes, cardiovascular disease and low energy among many people in developed nations is due to poor use of the calories contained in the products we consume, which are most of the time very high in fat. This metabolic deficiency or metabolic syndrome affects nearly 50 million Americans (nearly one American adult in four) and approximately 30 million Europeans. Roughly 7% of adults between 20 and 30 years of age and 40% of adults older than 40 years of age meet the criteria for developing this syndrome.

Metabolic syndrome represents a set of factors that occur simultaneously and increase the risk of cardiovascular disease, stroke and type 2 diabetes. Having only one of these factors—increase in blood pressure, high insulin level, excess fat around the waist or abnormal cholesterol level—increases the risk of contracting a serious illness; when several factors combine, the risk is even greater.

Fats, by their physical, chemical and physiological properties, play an important role in man's nutrition. In addition to the fats ingested by man in the form of food, the body itself manufactures lipids.

Dietary fats, and fats of adipose tissue, are primarily comprised of triglycerides. A triglyceride is a glycerol molecule with three fatty acids bound to it. Triglycerides are classified as lipids (fats), but only the three fatty acids are fats, as glycerol is a polyol that belongs rather to the class of carbohydrates. For example, glycerol is soluble in water and not in oil; glycerol is thus not a fat.

Differences in the structure of the fatty acids bound to glycerol make these fats different and influence their state of viscosity. There is thus a great diversity of triglycerides in foods such as olive, sunflower and soya oils, butter, tallow, lard, margarine, etc.

These fatty acids are assimilated in the intestine via a process common to all triglycerides which are not assimilable themselves.

They must be broken down into diglycerides, monoglycerides and free fatty acids by the action of lipases in the digestive tract; only these various products are assimilable, as triglycerides are not.

Lipolytic lipases or enzymes are enzymes secreted in the mouth, stomach and pancreas that cut triglycerides (TAG) into molecules small enough to be assimilable. Unfortunately, lipases attack triglycerides (TAG) only at positions 1 and 3 of the glycerol, leading to the formation of free fatty acids and 2-monoacylglycerol (glycerol molecule comprising one fatty acid bound at position 2).

If lipase activity is greater, even free fatty acids and glycerol can be obtained. All these molecules are assimilable by the body.

But it is there that things become complicated: as soon as these products are assimilated, the body resynthesizes (reforms) in the epithelial cells of the intestine (enterocytes) the triglycerides that had been broken down notably into free fatty acids and 2-monoacylglycerol by lipases such as pancreatic lipases (see FIG. 1 which represents the decomposition of triglycerides (triacylglycerol, TAG) by lipases, then triglyceride reformation in intestinal cells).

This triglyceride (TAG) reformation is achieved in particular by the activity of four enzymes (acyl-CoA synthetase, monoglyceride transacylase, diglyceride transacylase and diglyceride synthetase) which act as several stages of the synthesis.

Free fatty acids then will be bound to 2-monoacylglycerol in positions 1 and 3, which will reform triglycerides. These triglycerides, which are not soluble in the blood, will have to integrate chylomicrons which will evolve to VLDL, LDL and HDL and will transport throughout the body triglycerides (TAG), cholesterol and phospholipids.

These new triglycerides will thus be bound in lipoproteins and stored in adipocytes (fat cells). Triglycerides assimilated by the body, after being broken down into smaller fats, are again stored as triglycerides. Thus, the body does not use their energy immediately since they are stored in adipocytes. The body cannot metabolize fatty acids when they are bound to glycerol, as in triglycerides. To be metabolized, fatty acids must be free.

This metabolic deficiency, which some call the obesity gene (James V. Neel—*Diabetes Mellitus: a "thrifty" genotype rendered detrimental by "progress"*—American Journal of Human Genetics—vol. 14—pages 353-362), which constitutes the recomposition and storage of triglycerides, was an advantage for earliest man, thousands of years ago. Indeed, this ability to store fats was essential to survival. During prosperous periods, when hunting made it possible to kill game, men ate much and kept fats in reserve. The men, by storing fat in this way, could then survive long periods of famine by consuming their fat reserves during these hard times.

All this has been well explained by Stephen Cunnane in his book "The survival of the fattest," (*The Key to Human Brain Evolution*, World Scientific Publishing Co, New Jersey, United States, 2005, www.worldscibooks.com) which explains that people with the greatest fat reserves best survived long periods of food scarcity.

These are these same people who enriched their brain in omega-3 fatty acids and who became more intelligent and more advanced than their fellow creatures. During this period, metabolic deficiency was thus an evolutionary advantage, and was also an advantage in terms of natural selection. This is in particular the case in which *Homo sapiens* arose from primitive *Homo* species.

The example of the Melanesians is clear. These people left Taiwan on outriggers and then colonized all the Pacific Islands. Those who overcame the voyage were those with the greatest fat reserves.

Natural selection promoted survival of the largest, who then had children with the obesity gene. Thus 60-70% of Melanesians are type 2 diabetics.

But, today, in developed countries where hunger is sated perhaps in excess, this storage capability has become a catastrophe. Indeed, the resynthesis of triglycerides in enterocytes or intestine cells has disastrous consequences for the health of human beings. In particular, this triglyceride reformation induces:

- an increase in the size and number of chylomicrons, which transport triglycerides, cholesterol and phospholipids in the blood,
- an increase in the risks of atherosclerosis, facilitating the formation of arterial plaque and often arterial thrombosis, due to all the fatty acids trapped in triglycerides and not metabolized by the body,
- an increase in the level of bad cholesterol in circulation,
- an increase in the number and size of fat cells and thus the development of weight gain or obesity.

Furthermore, excess triglycerides in the blood reduce the quantity of free fatty acids available to be metabolized; thus, a shortage of energy.

Therefore, in certain serious cases, where the obesity gene is quite marked, even after a meal there is a feeling of not having nutrients available in the blood. This unpleasant feeling creates the desire to snack, a constant feeling of hunger that invites the consumption of food and drink in order to feel better.

This metabolic deficiency, the fact of not being able to use the calories contained in the fatty acids we assimilate, but which in triglyceride form are not usable, because the fatty acids are trapped therein, leads to a set of complications, called X syndrome by Reaven or "deadly quartet" by Kaplan

- G. M. Reaven—Stanford University School of Medicine—Division of Endocrinology, Gerontology and Metabolism, Department of Veterans Affairs Medical Center. Palo Alto, Calif., USA—*Syndrome X: 6 years later*—Journal of Internal Medicine 1994; 236 (Supplement 736): 13-22;
- G. M. Reaven—Simon & Schuster—Rockefeller Center, 1230 Avenue of the Americas—New York, N.Y. 10020—Syndrome X—Overcoming the silent killer that can give you a heart attack—Copyright 2000 G. M. Raven, T. Strom and B. Fox;
- Norman M. Kaplan MD—*The Deadly Quartet*—Arch Inter. Med—vol 149, July 1989: 1514-1520.

To find the energy it needs, our body, deprived of fatty acids available to be metabolized, will use glucose, which is omnipresent in the body. This is what makes us say that humans are hybrid vehicles. But glucose, in contrast to fatty acids, has many disadvantages:

- In burning, it releases only four calories per gram, whereas fatty acids release nine calories per gram,
- But above all, glucose, to be used and to penetrate cells, needs the hormone insulin. Also, for glucose to penetrate all its cells, the body must secrete even more insulin, beyond its capacities, and under extreme conditions. Thus at some point the body and in particular the pancreas can no longer secrete so much insulin, giving rise to the phenomenon of insulin resistance; glucose accumulates in the blood and can no longer penetrate the cells. This is called glucose intolerance; the body becomes insulin-resistant.

This hyperinsulinemia has perverse effects; too much insulin keeps fatty acids from exiting fat cells, which is called lipolysis. There is thus a still greater deficiency in fatty acids available to be used; since no more fatty acids are leaving fat cells, there is no possibility of losing weight notably for those suffering from obesity. Thus, the deficiency in available fatty acids is still greater, and glucose is used even more intensely in metabolism, from where still other complications arise, such as an increase in triglyceridemia and cholesterolemia.

All these metabolic disorders lead to dyslipidemia, hypertension, hyperuricemia and an above-normal glucose level since glucose poorly penetrates the cells and accumulates in the blood causing hyperglycemia.

All these metabolic complications can then lead to type 2 diabetes, which takes hold for the long term. An accumulation of fat in fat cells, in particular in the belly and around the waistline for men and in the buttocks for women, will also take hold for the long term.

All these metabolic problems will have repercussions on the spirits of the individual who is then often at a nadir which may lead to an emotional imbalance or a nervous breakdown in said individual suffering from these metabolic disorders, with notably a great feeling of dissatisfaction and constant hunger.

Moreover, the brain is thus poorly supplied. Excess insulin disrupts a number of blood parameters: adipocytokines, TNPβ, IL-6, PAI 1, adiposin, angiotensinogen, leptin, adiponectin, resistin, MCSF, TGFL, etc., increase in the blood. All these inflammatory products accentuate the biological disequilibria and destabilize the individual's lipid and carbohydrate metabolism.

Prior work sought new ways to short-circuit triglyceride synthesis and to overcome this metabolic deficiency.

Thus, various methods were found to destock fat cells and to make bioavailable the fatty acids stored in these fat cells.

Substances notably used to that end include flavonoid-rich tea extract to block the enzyme O'-methyltransferase which destroys adrenalin, or flavan-3-ol-rich grape seed extract and bioflavonoid-rich pine bark, the latter both increasing thermogenesis, i.e., releasing fatty acids from fat cells; similarly, polyphenols extracted from cocoa have the same effect.

It was to help release fats imprisoned by fat cells that heavy use was made of amphetamines and others isomerides or Mediator. But these products were very dangerous and all are now prohibited.

An attempt was also made to short-circuit fat cells with conjugated linoleic acid (CLA), which does not enter into the triacylglycerol (TAG) synthesis cycle, and with medium-chain oils that burn without passing through fat cells.

The Applicant sought to find a better means of confronting metabolic syndrome, fighting the obesity gene and using the energy of fats all while not promoting the formation of fat deposits.

The Applicant noted that many laboratories proposed the use of lipase-blocking agents in order to prevent TAG decomposition and reformation.

But, the Applicant discovered in a surprising manner that anti-lipase products were absolutely not effective in losing weight, and in reality had a harmful action on the body by increasing the quantity of TAG remaining in the intestine.

The solution proposed by the present invention is to inhibit, reduce and/or prevent the reformation of triglycerides in the enterocytes or cells of the intestine of the body by the use of a combination of proteolytic enzyme or protease with at least one lipolytic enzyme or lipase.

By administering such proteolytic enzymes, especially lipases, triglyceride resynthesis is avoided in an elegant fashion and with no danger to the body.

Thus, the Applicant discovered that:

proteolytic enzymes disrupt the activity of the four enzymes (acyl-CoA synthetase, monoglyceride transacylase, diglyceride transacylase and diglyceride synthetase) in the enterocyte, which help triglyceride resynthesis, but especially if particular lipases that act advantageously at position 2 on triglycerides of the intestine are used, 2-monoacylglycerol production is reduced, which is the pivot of triglyceride resynthesis. This metabolic pathway is known by all biochemists as being the synthesis pathway of 80% of triglycerides; the other, less-efficient pathway is resynthesis from glycerol-3-phosphate and only produces 20% of triglycerides.

The present invention thus has as an object a composition comprising a combination of at least one proteolytic enzyme or protease and at least one lipolytic enzyme or lipase for its use in preventing the synthesis or the reformation of triglycerides, notably in the enterocytes or cells of the intestine, advantageously by degrading 2-monoacylglycerol.

Advantageously according to the present invention, the proteolytic enzyme is selected from the group comprising subtilisin, nagarse, nattokinase, chymotrypsin, trypsin, elastase, thermolysin, serrapeptase, and mixtures thereof.

In a particularly advantageous manner according to the present invention, the proteolytic enzyme is subtilisin or nattokinase or a mixture of subtilisin or nattokinase with one or more other proteolytic enzymes.

According to a particular characteristic of the present invention, the proteolytic enzyme is present in a proportion of 5-30% by weight, typically 10-20% by weight, in relation to the total weight of the composition.

According to another particular characteristic of the present invention, the lipolytic enzyme is present in a proportion of 70-95% by weight, typically 80-90% by weight, in relation to the total weight of the composition.

Advantageously according to the present invention, the composition enables the administration of a daily dose of proteolytic enzyme ranging between 10 mg and 200 mg, more particularly between 10 mg and 100 mg, typically between 20 mg and 100 mg, for example between 50 mg and 100 mg.

Advantageously according to the present invention, the composition enables the administration of a daily dose of lipolytic enzyme ranging between 100 mg and 400 mg, more particularly between 100 mg and 300 mg, typically between 100 mg and 200 mg or 200 mg and 300 mg.

In a particular embodiment of the present invention, the composition is formulated to be administered orally.

Advantageously according to the present invention, the composition is provided in the form of a hard or soft capsule, tablet, granule, powder or oral solution.

According to a particular characteristic of the present invention, the composition is provided in the form of a hard or soft capsule or a gastro-resistant tablet.

Advantageously, the composition is gastro-resistant so that the composition releases the proteolytic enzyme and the lipolytic enzyme in the intestine.

In an advantageous manner according to the present invention, the composition is a pharmaceutical, cosmetic, nutraceutical or dietary composition, a dietary supplement, or a medical device, and can comprise any carrier or suitable excipient, acceptable from a pharmaceutical, cosmetic, dietary or nutraceutical point of view, as well as conventional additives, known to the person skilled in the art.

In an advantageous manner according to the present invention, the composition comprises at least one lipase, such as a lipase extracted from *Thermomyces lanuginosus, Rhizopus niveus, Penicillium roqueforti, Penicillium camemberti, Geotrichum candidum, Candida rugosa, Candida lipolytica, Candida parapsilosis, Aspergillus niger, Rhizopus oryzae, Mucor javanicus*, or a lipase from *Candida antarcitica, Geotrichum candidum* or a lipase extracted from oats, as well as mixtures thereof.

In a particularly advantageous manner, the composition comprises several lipases.

Advantageously, the lipases used in the context of the present invention are active at position 2 on the triglycerides and will reduce 2-monoacylglycerol and prevent triglycerides from forming again, a pathway that produces 80% of triglycerides.

According to a particular characteristic of the invention, the composition comprises at least one lipase selected from the group comprising Cal A or Cal B lipase of *Candida antarctica, Geotrichum candidum, Candida rugosa*, and binary or ternary mixtures of these lipases. Typically, the composition comprises a mixture of Cal A or Cal B of *Candida antarctica, Geotrichum candidum* and *Candida rugosa*.

In a particular embodiment, the composition of the present invention is intended for use in preventing or reducing excess weight, adipogenesis or excess cholesterol, or as an anti-cellulite agent, typically in a cosmetic composition or a medical device.

In another particular embodiment, the composition or the product of the present invention is intended for use in preventing or treating obesity or atherosclerosis, or cardiovascular disorders, or type 2 diabetes, and in general what is referred to as metabolic syndrome, to fight the obesity gene.

The present invention also has as an object a composition or a product containing:
  at least one proteolytic enzyme, such as subtilisin, and
  at least one lipase, such as a Cal A or Cal B lipase of *Candida antartica, Geotrichum candidum*, a *Candida rugosa* lipase, or a binary or ternary mixture of these lipases,
as a combination product for simultaneous, separate or staggered use to prevent the synthesis of triglycerides, advantageously by degrading 2-monoacylglycerol in the intestine.

Advantageously according to the present invention, the proteolytic enzyme is selected from the group comprising subtilisin, nagarse, nattokinase, chymotrypsin, trypsin, elastase, thermolysin, serrapeptase, and mixtures thereof.

In an advantageous manner according to the present invention, the lipase is extracted from *Thermomyces lanuginosus, Rhizopus niveus, Penicillium roqueforti, Penicillium camemberti, Geotrichum candidum, Candida rugosa, Candida lipolytica, Candida parapsilosis, Aspergillus niger, Rhizopus oryzae, Mucor javanicus*, or is extracted from *Candida antarctica, Geotrichum candidum* or from oats.

The proteases are typically administered in the form of a gelatin capsule. The proteases are advantageously administered two to three times per day, one gelatin capsule with each meal.

Typically, the product comprises at least one lipase of *Candida antarctica* such as lipase Cal A or Cal B of *Candida antartica*, a *Geotrichum candidum* lipase, a *Candida rugosa* lipase and/or a lipase extracted from oats. This is particularly advantageous because these lipases act at position 2 on the triglycerides and thus break down 2-monoacylglycerol and help proteases prevent triglycerides from reforming in the body. Without 2-monoacylglycerol, TAG resynthesis is much more difficult (remember that this pathway produces 80% of the TAG in the body).

The lipases are typically administered in the form of a gelatin capsule. The lipases are advantageously administered three times per day, one gelatin capsule with each meal.

In a particular embodiment, the composition or the product of the present invention is intended for use as a drug, cosmetic agent, medical device, dietary composition, nutraceutical or dietary supplement.

In a particular embodiment, the composition or the product of the present invention is intended for its use in preventing or reducing excess weight, adipogenesis or excess cholesterol, or as an anti-cellulite agent.

In another particular embodiment, the composition or the product of the present invention is intended for its use in preventing or treating obesity, atherosclerosis, cardiovascular disorders, or type 2 diabetes, and in general what is referred to as metabolic syndrome, in order to fight the obesity gene.

Figure 1:
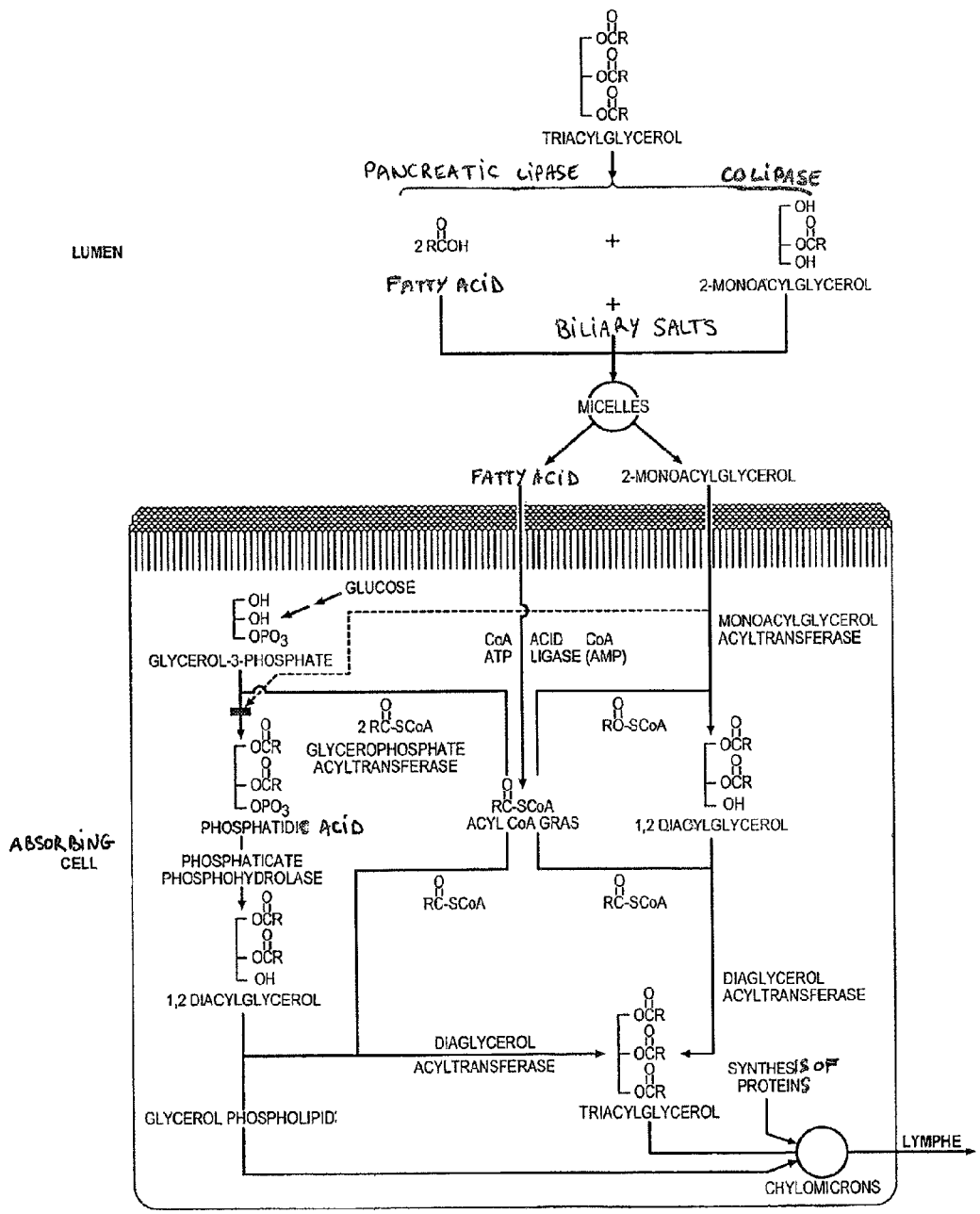
FIG. 1 depicts the metabolism of triacylglycerol in humans.

The following examples are intended to illustrate the invention without limiting its scope in any way.

EXAMPLE 1

Study of the Activity Induced by the Administration of a Combination of Proteolytic Enzymes, Such as Subtilisin, and Lipolytic Enzymes, Such as Cal A of *Candida antartica, Geotrichum candidum* Lipase, and *Candida rugosa* Lipase, to Prevent Triglyceride Synthesis An activity and test dose study was carried out using rats. These rats were divided into three groups (test conditions) of 10.

The first condition, the control group, did not receive any active product.

The other two conditions, each comprising groups of 10 rats, received for 8 days (once per day), respectively, a mixture of 50 mg of subtilisin and 100 mg of Cal A lipase of *Candida antartica* for group 1, and a mixture of 50 mg of subtilisin and 50 mg of *Geotrichum candidum* lipase, as well as 50 mg of *Candida rugosa* lipase for group 2.

After 8 days, all the rats, including the control group, received a dose of olive oil equivalent in man to a tablespoon (15 ml).

After this administration of olive oil to all the rats, blood was sampled from all the animals 1 hour, 2.5 hours and 5 hours after administration of the olive oil. Triglyceride levels were then calculated from the sampled blood.

In the control rats, a high amount of TAG in the blood was found, for the three samples (1 h, 2.5 h and 5 h).

Groups 1 and 2 did not have TAG in the blood.

Olive oil was then administered twice again at a one-week interval—conditions 1 and 2 all the while continuing to receive subtilisin in combination with the lipases mentioned above.

The results were the same these two other times.

TAG did not reform in groups 1 and 2, whereas the control group had a high concentration of TAG in the blood, for the three samples.

It can thus be concluded that the combination of subtilisin and lipases prevented the formation of triglycerides (TAG).

EXAMPLE 2

Study of 10 Miniature Pigs

A study was carried out on 10 miniature pigs.
These pigs were separated into four groups:
one control pig
three pigs in group 1
three pigs in group 2
three pigs in group 3
The control pig did not receive enzyme.

The three other conditions received three formulas of enzymes.

Formula 1 was composed of 10 mg of subtilisin and 300 mg Cal A lipase, as well as pancreatin. It was administered to the pigs of group 1 at a dose of 20 mg/kg.

Formula 2 was composed of 10 mg of subtilisin and 300 mg of *Candida rugosa* lipase, as well as pancreatin. It was administered to the pigs of group 2 at a dose of 40 mg/kg.

Formula 3 was composed of 10 mg of subtilisin and 300 mg of *Geotrichum candidum* lipase, as well as pancreatin. It was administered to the pigs of group 3 at a dose of 40 mg/kg.

The formulas were given for 8 days, once per day.

The results (triglyceride levels) were measured in blood samples taken every 2 hours for 2 days.

Figure 2:
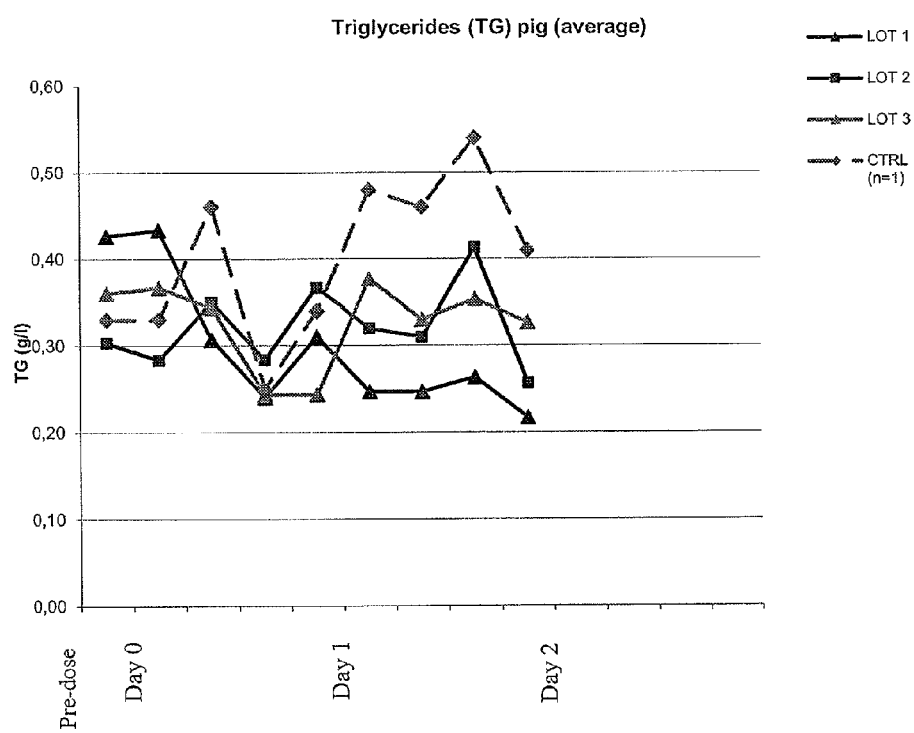
FIG. 2 summarizes the results of example 2. The scheme represents the triglycerides level (in g/l) as a function of time after administration of compositions according to the present invention. LOT 1=Group 1, LOT 2=Group 2, LOT 3=Group 3, CTRL=control group.

The results of the study showed that the control pig produced an abundance of triglycerides, whereas pigs in the other three conditions produced relatively few triglycerides (see FIG. 2).

A second study was carried out 8 days later using this time as control animals one pig from each condition mentioned above (one pig from group 1, one pig from group 2 and one pig from group 3).

The two remaining pigs per batch received the same enzyme formulas as those mentioned above.

It was then noted that none of the pigs produced many triglycerides, including the control pigs. It can thus be concluded that the enzymes given 8 days earlier still had activity in the blood with a delayed effect, and that lipoproteins were reduced in the control animals which had received the enzymes 8 days earlier.

The invention claimed is:

1. A method for inhibiting or reducing synthesis or reformation of triglycerides which comprises:
   administering to a patient suffering from excess weight or obesity, a composition comprising a combination of at least one proteolytic enzyme and at least one lipase to reduce excess weight, treat or reduce obesity in the patient,
   wherein the proteolytic enzyme is subtilisin and the lipase is a lipase derived from *Geotrichum candidum*, a lipase derived from *Candida rugosa*, a Cal A or Cal B lipase derived from *Candida Antarctica*, or a mixture of these lipases, and wherein the inhibition or reduction of the synthesis or reformation of triglycerides is carried out by degrading 2-monoacylglycerol in the enterocytes or the cells of the intestine,
   wherein the at least one lipase is administered at a daily dose of 100-400 mg, and
   wherein the at least one proteolytic enzyme is administered at a daily dose of 10-200 mg.

2. The method of claim 1, wherein the composition is in the form of a drug, cosmetic agent, medical device, dietary composition, nutraceutical or dietary supplement.

3. The method of claim 1, wherein the composition is administered orally.

4. The composition of claim 1, wherein the composition is in the form of a hard or soft capsule, tablet, granule, powder or oral solution.

5. The method of claim 4, wherein the composition is in the form of a gelatin capsule or a gastro-resistant tablet.

6. The method of claim 1, wherein the administration of the composition includes a daily dose of proteolytic enzyme of 50-100 mg.

7. The method of claim 1, wherein the administration of the composition includes a daily dose of lipase of 200-300 mg.

8. A method for inhibiting or reducing synthesis or reformation of triglycerides which comprises:
    administering to a patient suffering from excess weight or obesity a product for inhibiting or reducing synthesis or reformation of triglycerides lipase to reduce excess weight, treat or reduce obesity in the patient,
    said product comprising:
    a first compositions comprising at least one proteolytic enzyme, wherein the proteolytic enzyme is subtilisin, and
    a second composition comprising at least one lipase, wherein the lipase is a lipase derived from *Geotrichum candidum*, a lipase derived from *Candida rugosa*, a Cal A or Cal B lipase derived from *Candida antarctica*, or a mixture of these lipases,
        wherein the proteolytic enzyme and the lipase are administered simultaneously, separately or sequentially, and
        wherein the inhibition or reduction of the synthesis or reformation of triglycerides is carried out by degrading 2-monoacylglycerol in the enterocytes or the cells of the intestine, and
    wherein the at least one lipase is administered at a daily dose of 100-400 mg, and wherein the at least one proteolytic enzyme is administered at a daily dose of 10-200 mg.

9. The method of claim 8, wherein the composition is in the form of a drug, cosmetic agent, medical device, dietary composition, nutraceutical or dietary supplement.

10. A method for treating or reducing obesity, or reducing excess weight, said method comprising:
    administering to a patient in need thereof a composition comprising a combination of at least one proteolytic enzyme and at least one lipase, wherein the proteolytic enzyme is subtilisin and the at least one lipase specifically acts on position 2 of the triglyceride and is a lipase derived from *Geotrichum candidum*, a lipase derived from *Candida rugosa*, or a mixture of these lipases.

11. A method for treating or reducing obesity, or reducing excess weight, said method comprising:
    administering to a patient in need thereof a product comprising:
    a first composition comprising at least one proteolytic enzyme, wherein the proteolytic enzyme is subtilisin, and
    a second composition comprising at least one lipase, wherein the lipase specifically acts on position 2 of the triglyceride and is a lipase derived from *Geotrichum candidum*, a lipase derived from *Candida rugosa*, or a mixture of these lipases,
    wherein the proteolytic enzyme and the at least one lipase is administered simultaneously, separately or sequentially.

* * * * *